United States Patent [19]
Berry

[11] Patent Number: 5,869,072
[45] Date of Patent: Feb. 9, 1999

[54] METHOD FOR THE PRODUCTION OF A GLOVE

[76] Inventor: Craig J. Berry, 2 Taylor La., Westport, Conn. 06880

[21] Appl. No.: 897,583

[22] Filed: Jul. 21, 1997

[51] Int. Cl.$^6$ ...................................................... A61F 13/00
[52] U.S. Cl. .............................. 424/402; 424/443; 2/159; 2/161.7; 2/169
[58] Field of Search ................................... 424/401, 443, 424/447, 449; 2/159, 161.7, 169

[56] References Cited

U.S. PATENT DOCUMENTS

| | | | |
|---|---|---|---|
| 4,643,791 | 2/1987 | Jurrius et al. | 156/251 |
| 4,942,153 | 7/1990 | Fernandez | 514/2 |
| 4,978,526 | 12/1990 | Gesslein et al. | 424/70 |
| 5,026,552 | 6/1991 | Gueret et al. | 424/401 |
| 5,554,363 | 9/1996 | Nandagiri et al. | 424/70.51 |
| 5,607,921 | 3/1997 | Bernard et al. | 514/23 |
| 5,643,601 | 7/1997 | Gross et al. | 424/450 |
| 5,660,840 | 8/1997 | Pruett | 424/401 |
| 5,705,166 | 1/1998 | Arve | 424/401 |

Primary Examiner—Thurman K. Page
Assistant Examiner—Lakshmi S. Channavajjala
Attorney, Agent, or Firm—H. Gibner Lehmann; K. Gibner Lehmann

[57] ABSTRACT

A therapeutic applique for treatment of dry hands, either as a patch, face mask, or glove. The applique has the form of a porous, flexible sheet that is applied to the skin, and the sheet has a water-activatable material carried on its surface and also permeating its pores. The water-activated material, when in a dry, inactive state, preferably has a moisture content of less than 10% by weight, of the sheet, and is soluble in water. The arrangement is such that when the applique is applied to the skin, along with water, the applique's water-soluble component partially disassociates from it and leaches onto the skin, either while the sheet is in place on the skin or prior to the sheet being placed on the skin. In addition, with time the outermost layer of the water-soluble component undergoes evaporation, causing it to partially re-solidify, thereby forming an occlusive outer barrier which tends to retain the remaining water-soluble components between itself and the skin. There results improved, all natural skin moisturization, without preservatives and without undesirable greasy or oily residue being left on the skin.

12 Claims, 2 Drawing Sheets

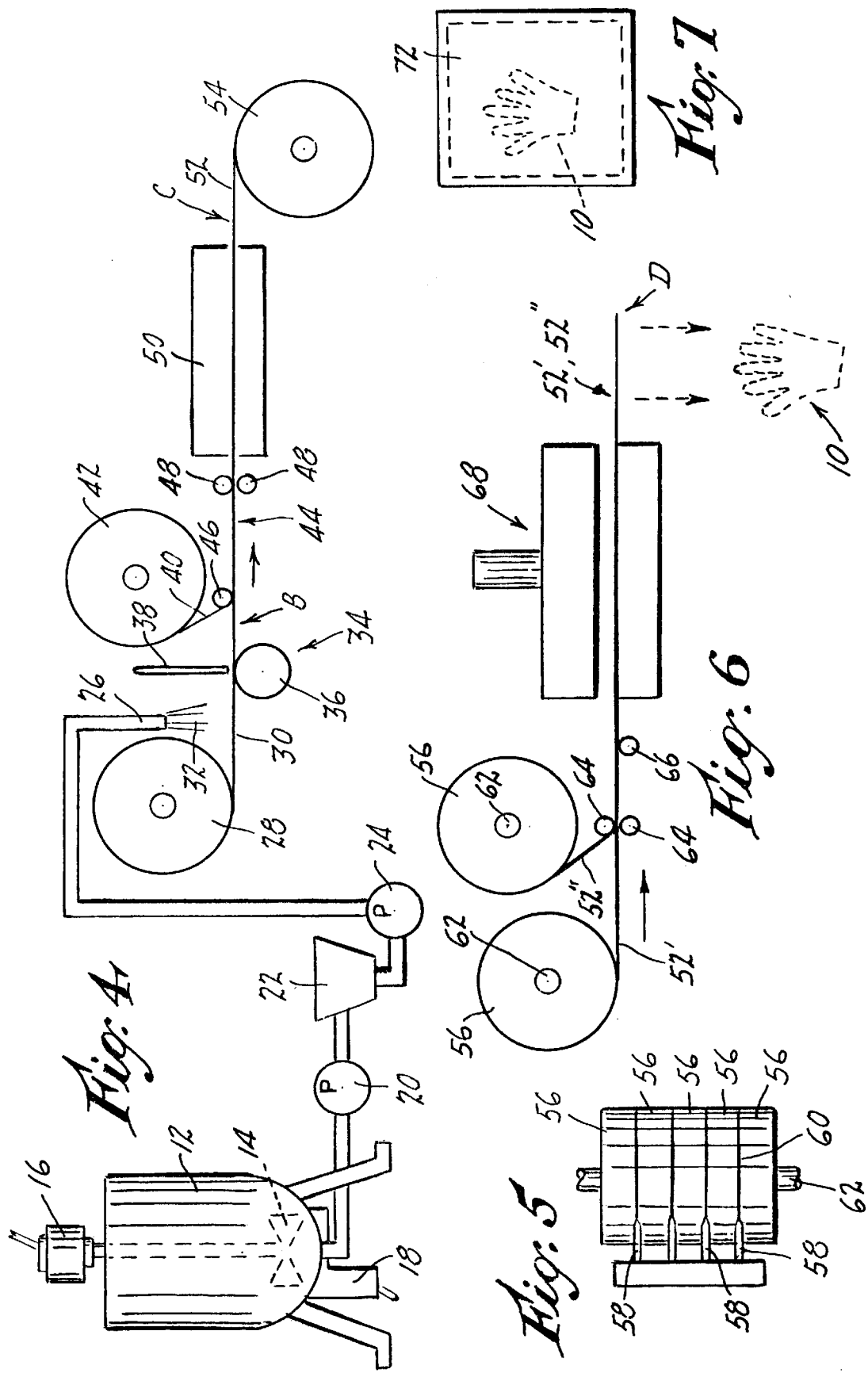

METHOD FOR THE PRODUCTION OF A GLOVE

NO CROSS REFERENCES TO RELATED APPLICATIONS

STATEMENT AS TO RIGHTS TO INVENTIONS MADE UNDER FEDERALLY-SPONSORED RESEARCH AND DEVELOPMENT

Research and development of the present invention and application have not been Federally-sponsored, and no rights are given under any Federal program.

BACKGROUND OF THE INVENTION

Field of the Invention

This invention relates generally to products for treatment of dry skin, particularly dry skin on the hands and face. It also relates to a method for using such products, and a method for manufacture thereof.

Description of the Related Art Including Information Disclosed under 37 CFR Sections 1.97–1.99

The problem of dry skin has today, become almost universal. There is a multitude of skin care products on the market, including various types of creams, lotions and oils.

In the decades subsequent to 1940, lotions incorporating homogenized oil-water mixtures were developed, the theory being that the water was, at least in part, absorbable into the skin, with the oil remaining on the skin so as to form a barrier. It was considered that the barrier restricted the inevitable evaporation which occurred, but in practice, evaporation was found to be an ongoing process, and the results obtained were marginal, at best.

Also, all oil-based moisturizers suffered from a significant disadvantage, namely that of imparting to the skin, a residual, greasy feel and appearance.

Subsequent discoveries included lotions containing urea, which is hygroscopic, thus having the ability to absorb and hold water in place on the skin itself. An undesirable side effect included inadvertent irritation to the skin, due to the fact that urea was somewhat on the base side, pH wise, and was capable of forming salts only when combined with relatively strong acids.

Other ventures involved the use of lecithin, a naturally occurring substance derived from soybeans. Lecithin is generally considered a phospholipid, and is capable of absorbing relatively large amounts of water. A preparation containing lecithin is purportedly sold under the trademark COMPLEX 15, manufactured by Key Pharmaceuticals.

Still other compounds involved the use of emulsions containing water, glycerine, mineral oil, alcohol, propylene glycol, lanolin, and fatty acids. Additional products comprise preparations containing what is known as Retin-A, a vitamin A derivative.

A-hydroxy-acids have also been used for skin treatment. While this class of product is often referred to as a moisturizer, in fact, the action of the A-hydroxy-acid is actually one involving a mild attack on the skin, wherein the outermost cells, which are likely to be the oldest and most dried-out, are chemically removed. The remaining cells, previously lying below the outer layer, then become the new outer layer. Naturally, these new cells, being younger and more protected, yield the desired result, namely a "new" skin look and feel, as well as increased moisture content, at least for the period immediately following the use of the A-hydroxy-acid.

Other methods of treatment involved what are known as "peeling agents", such as benzoyl peroxide; astringents, which firm up the tissues of the skin; and in some cases, oral or topical antibiotics, where infection is suspected to be a problem.

U.S. Pat. Nos. 4,591,501 and 5,302,377 are directed to related objectives in the treatment of dry skin.

In particular, U.S. Pat. No. 4,591,501 relates to a film that is produced by applying to a suitable base paper or material, a polypeptide, a plasticizer, and a polymer. The film, when moistened, will release the polypeptide and enable it to cover the skin. The nature of the polypeptide utilized is given in col. 1, line 61, namely, "'Polypeptide' as used herein, means and refers to polyamino acids derived from protein along with the proteins themselves. The polyamino acids useful in the practice of the invention are those . . . having a molecular weight of at least 3000. Preferably, the polyamino acids are derived from collagen."

Specific reference is made to the large amount of prior art cited during the prosecution of the application which matured into U.S. Pat. No. 4,591,501.

U.S. Pat. No. 5,302,377 relates to lotions for use as cold creams, after shaves, anti-perspirants, skin moisturizers, and related products. More particularly the patent involves a topical preparation of a fatty alkoxylate ester. The patentee claims that use of the preparation as an emollient, to smooth and soften skin, is superior to some prior known techniques, in that there is little or no oily or greasy feel experienced by the user, and thus the product is aesthetically more acceptable.

Finally, most of the creams and lotions on the market today utilize, of necessity, a preservative of some type, which can be irritating to the skin of the user. In essence, a preservative is a chemical that kills or controls bacteria, and the application of such a compound to the skin, while deemed acceptable in limited amounts, is considered a potential hazard over the long term. An example of a preservative widely used is methylparaben, which is a crystalline compound, $HOC_6H_4\text{-}COOCH_3$; it is the methyl ester of parahydroxybenzoic acid. Also, propylparaben is frequently used as a preservative. It is a crystalline ester, $HOC_6H_4\text{-}COOC_3H_7$; it is sometimes referred to as propyl parahydroxy-benzoate.

A good number of "moisturizers" currently being marketed in this country, are known to contain propylparaben.

Failure to include a preservative in sufficient quantity to control bacterial growth can have serious consequences, as can well be appreciated when it is considered that skin care products are used by persons from infancy, through the geriatric stage. This latter group is most susceptible to adverse side effects, and it is considered that wherever possible, use of preservatives in products which are ingested or topically applied, should be minimized to the greatest possible extent, since the potential hazardous long-term effects of chemicals in our environment is only recently, within the last decade or so, being considered to any great degree.

Also, with most lotion/cream products, it is necessary to apply the substance and usually leave it on all day. With greasy formulations, this leads to inadvertent soiling of papers that may be handled, as during office work. Products applied at bed time tend to be rubbed off onto the linens, as the user continuously and unconsciously shifts position during sleep.

Accordingly there has existed a long-felt need for a product which can be applied to the skin for a relatively short time interval and without leaving a greasy look or feel to the skin, and while still performing its intended moisturizing function.

SUMMARY OF THE INVENTION

The above disadvantages and drawbacks of prior skin care products are largely obviated by the present invention, which has for one object, to provide a novel and improved skin applique which is extremely simple in its structure, and which is both effective and convenient in use.

Still another object of the invention is to provide an improved skin applique as above outlined, which contains ingredients that are substantially completely natural and non-toxic.

A related object of the invention is to provide an improved applique of the kind indicated, which does not utilize preservatives of any kind.

Still another object of the invention is to provide an improved applique in accordance with the foregoing, which is completely chemically inactive during storage and shipping, and which is purposefully activated solely just prior to the use of the product by the consumer.

A further object of the invention is to provide an improved applique as above characterized, which has an extended shelf life, due to the inherently inactive nature of the product.

Still another object of the invention is to provide an improved applique as noted above, which can be inexpensively packaged in a watertight pouch, and sold in multiple units containing a plurality of individual pouches, each being wholly self-contained and totally inactive until just prior to use by the consumer.

The above objects are accomplished by a therapeutic applique for treatment of dry hands, comprising in combination a porous, flexible sheet to be applied to the skin, and a water-activatable material carried on a surface of the sheet and permeating the pores thereof, the water-activated material having a moisture content of substantially less than 10% by weight, of the sheet, and wherein the material is soluble in water, so as to partially disassociate from the sheet and leach onto the skin of the user when water is brought into contact with the sheet, either while the sheet is in place on the skin or prior to the sheet being placed on the skin.

The objects are further accomplished by a method of manufacturing a therapeutic glove for treatment of dry hands, comprising the steps of mixing a quantity of water with polyvinyl alcohol, and heating the mixture so as to dissolve the polyvinyl alcohol in the water, wetting a porous sheet with the mixture of polyvinyl alcohol and water, heating the sheet so as to reduce the water content to substantially less than 10% by weight of the sheet and to convert the polyvinyl alcohol to a solid state, superposing the sheet on a second sheet so as to form a double layer thickness, and cutting the superposed sheets and joining edge portions thereof to form the shape of a glove. The method further includes packaging the glove in a container, to minimize its exposure to moisture, and thereby maintain the solid polyvinyl alcohol in a dry, inactive state, until the glove is ready to be removed from the container and applied to the hand of the user.

The objects are further accomplished by a method of imparting moisture to the hands of a person having dry skin, comprising the steps of forming a glove of porous material, and impregnating the glove with a quantity of polyvinyl alcohol, thereafter heating the glove and impregnated polyvinyl alcohol, so as to reduce the water content of the glove to an extent sufficient to solidify the polyvinyl alcohol on the surfaces and in the pores of the glove, and applying the glove to the hand. The method further embraces the step of applying water to the exterior of the glove so as to partially dissolve the polyvinyl alcohol and allow it to directly contact and saturate the skin of the hand, for an extended length of time.

The arrangement is such that as the outer portions of the polyvinyl alcohol/water mixture evaporate, they form an occlusive barrier layer which in effect, traps moister, inner portions of the mixture and keeps these inner portions in continual contact with the skin, to optimize water transfer thereto.

Other features and advantages will hereinafter appear.

BRIEF DESCRIPTION OF THE DRAWINGS

In the drawings, illustrating a preferred embodiment of the invention:

FIGS. 4–6 are diagrammatic representations showing various steps in the preparation of the water-activatable, moisturizing applique of the present invention, and FIG. 7 is a plan view of a moisture-tight container or pouch, used to store the appliques of the invention and maintain the water-active component of the appliques in an inactive state during storage and shipping, until just prior to use by the consumer.

DESCRIPTION OF THE PREFERRED EMBODIMENTS

The present invention involves essentially the production and use of an applique that is intended to be placed onto the skin of a person, the applique preferably taking the form of a simple single-layer patch which may be of generally kidney-shape or other outline, or alternately a face mask or a glove. The skin is preferably wetted just prior to application, such that the applique will adhere to it, as will be described below.

In the case of the glove, it is preferable to first don the glove and thereafter apply water sparingly, which will cause a normally inactive component of the glove to partially dissolve and conform to the contours of the hand in such a manner as to expose most areas of the hand to the water-dissolved component.

Figure 1:
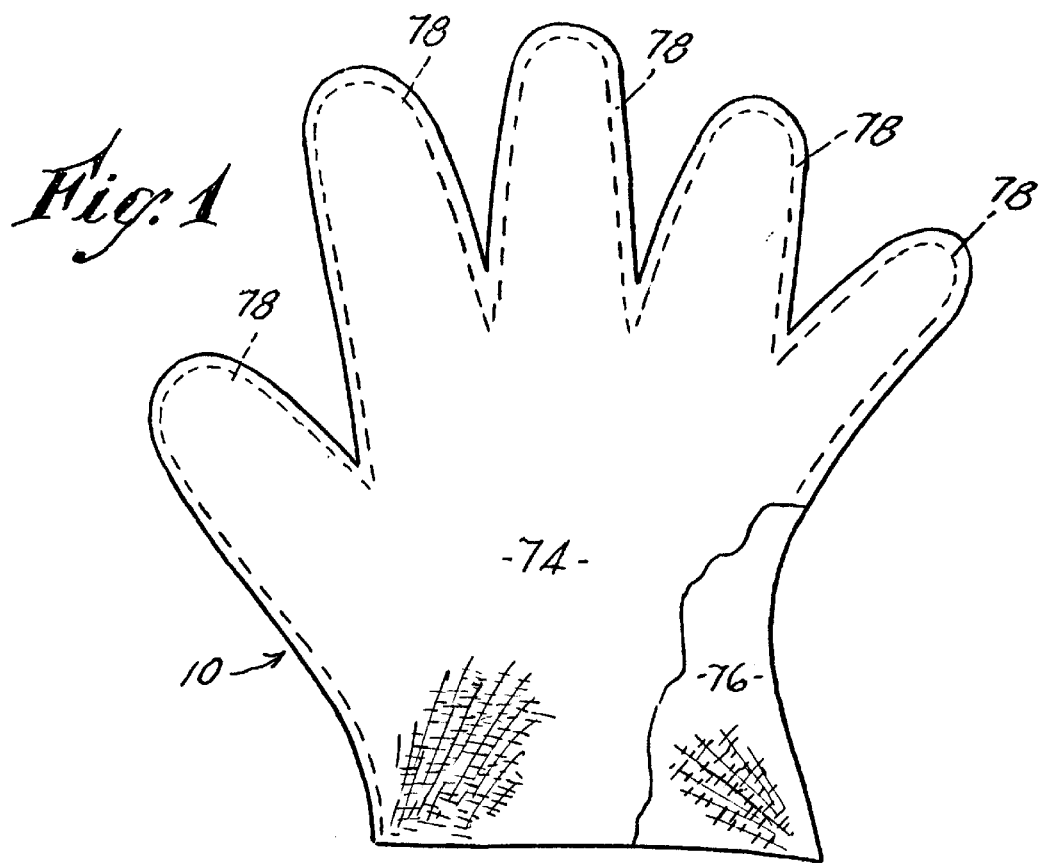
FIG. 1 is a plan view, partly broken away, of a water-activatable moisturizing glove constructed in accordance with the principles of the present invention.

As an example of the fabrication of the skin-care glove of the invention, reference is made to FIGS. 4–6. A glove constructed in accordance with the invention is illustrated in FIG. 1 and designated by the numeral 10. In FIGS. 4–6, the process of manufacture of a glove in accordance with the invention is essentially as follows:

A vat or tub generally designated 12 is filled with a quantity of cold water along with pellets of polyvinyl alcohol, which may be of a type sold under the Trademark AIR VOL 523. Typically, the percentage by weight of the polyvinyl alcohol is 15% of the total weight of the mixture of polyvinyl alcohol and water. The pellets are small in size, sufficiently so to be characterized as granular in nature. As the pellets are being introduced into the vat 12, a paddle 14 is activated via an electric motor 16 to stir the polyvinyl alcohol and water, and in addition, the vat is heated by a heater 18 up to a temperature on the order of 140–165 degrees F., for a period of up to 3–4 hours, depending on the time required for the polyvinyl alcohol pellets to completely dissolve in the hot water.

When all of the polyvinyl alcohol pellets have gone into solution in the water, the mixing is halted.

The resulting solution in the vat 12 is then pumped, via a first pump 20, to a trough 22, for temporary storage. An additional pump 24 draws the solution from the trough 22, to a distribution nozzle or head 26, which preferably emits a spray across the sheet 30 which is disposed immediately below. A supply roll 28 of silicone-coated backing paper is provided, with the backing paper or sheet 30 that is drawn off the roll being coated with a slurry or slush 32 of polyvinyl alcohol and water, the sheet 30 thereafter extending to a knife-over-roller apparatus, generally designated 34, and comprising a rotating roller 36 and doctor blade 38. The spacing between the roller 36 and lower edge of the doctor blade 38 is on the order of 2–3 mils or so, resulting in a uniform spreading of the polyvinyl alcohol and water mixture on the backing paper or backing sheet 30 at the location of the arrow B. Thus the solution from the nozzle 26 is spread over the backing paper 30. The quantity of polyvinyl alcohol and water at the location B is such that after the sheet is dried, a thickness of solid, dried polyvinyl alcohol on the order of 2.5 mils or so is obtained.

Following the processing at the knife-over-roller apparatus 34, a sheet 40 of mesh or scrim from a supply roll 42 is laid over the wet-coated sheet 30 of backing paper, as in FIG. 4. The scrim 40 may be nylon or other plastic-type composition, having a pore size on the order of several mils or more. The layer of wetted backing paper 30 and scrim 40 constituting an assemblage 44, are joined under a positioning roller 46, and travel past additional rollers 48, to a furnace 50, comprising a series of drying ovens, typically three in number. These heat the superposed layers 30, 40 and remove a large part of the water content, leaving a combined backing paper-scrim/polyvinyl alcohol-water composite sheet assemblage 52 having an overall water percentage, by weight, of preferably less than 10 percent, at the location indicated by the arrow C.

The dried sheet assemblage 52 is drawn from the ovens to a take up roll 54, for temporary storage.

Referring now to FIG. 5, one such roll 54 is shown, typically 52½ inches in width. The next step, according to the invention, involves cutting the roll 54 into five separate rolls 56 each about 10½ inches in width. This is preferably done by suitable knives 58, which slit completely through the 52½ inch roller at four equally spaced locations, corresponding to the cuts 60 shown in FIG. 5.

Referring now to FIG. 6, two 10½ inch rolls are selected from the five rolls 56, and are mounted on spindles 62, respectively. A sheet 52" from one roll 56 meets the sheet 52' from the other roll 56, and the sheets become superposed, as they pass between rollers 64 and to roller 66, and thereafter enter a combined die-cutting and heat-fusing station 68, where two functions are carried out. The die portion of the station 68 cuts a blank from the superposed sheets 52', 52", in the form of the article ultimately being produced, in the present example, the glove 10 shown in FIG. 1. Simultaneously, the edge portions around all five fingers of the glove 10 are heat-fused to one another in the station 68, by melting the material of the mesh 40. The sheets 52', 52" exit the die-cutting and heat-fusing station 68, and the blank, constituting the glove 10 either drops out of the sheet or is manually removed therefrom. The remaining sheet material (which originally surrounded the glove, indicated by the arrow D) is discarded as scrap. FIG. 6, shows, in dotted outline, a glove as it is separated from the sheet. There is then removed from each glove, the two pieces of silicone-coated backing paper, now designated 70, which originally were part of the original carrier sheet 30 in FIG. 4.

Preferably, the glove is then inserted in a laminated, metallic-foil backed, water- and moisture-impervious pouch 72, FIG. 7, and sealed therein, for shipment to a store, and subsequent purchase by the consumer. The pouch 72 can have a foil thickness of 3.5 mils, and a suitable backing material for the foil of the pouch can be polyethylene.

The finished glove 10 in FIG. 1 comprises two layers of mesh or scrim, an upper palm panel or layer 74 and a lower back-of-the-hand or layer 76. The scrim is heat fused at the borders 78 of all five fingers, shown in dotted outline. The mesh layers have a coating of dried polyvinyl alcohol, as well as one or more optional components, which can be included, to be described below.

In use, the glove can be applied to one hand by first wetting the hand with luke warm water, and applying the glove with the free hand. Any creases or bubbles in the glove layers can be smoothed out by lightly tapping with the finger tips of the free hand, optionally pre-moistened. The glove exterior is then preferably gently misted with an atomizer sprayer. Any extra length in the fingers of the glove that extends past the wearer's finger nails can be folded back over the nails, to produce a double layer glove thickness, and correspondingly increased water retention in this area.

As the glove which is being worn is moistened, most or all of the polyvinyl alcohol coating (which was present on the dry glove) dissolves, leaving mixture of dissolved polyvinyl alcohol and water, held captive in the mesh in a somewhat slurry or slush form, by capillarity. Furthermore, as the outermost part of the slurry begins to dry by normal evaporation, the inner parts of the slurry disposed between this outer part and the skin, continue to moisturize the skin, because the outer, drying layer forms, in effect, an occlusive or barrier layer. This leads to improved penetration of the moisture underlying the barrier layer and into the skin.

Optionally, one hand can be treated at a time. Alternately, the formerly free hand can be treated, by donning a second glove (dry condition) in an analogous manner. It is preferable to wear the gloves for between 30 and 45 minutes, and re-moisten them every 15 minutes or so, either with droplets from a faucet, or with a spray mister.

To remove the gloves, the wrist portions can be merely peeled off. Placing the hands in warm water just prior to such peeling off may also facilitate this process.

In the case of severely dry hands, re-application of new gloves can be undertaken as often as desired, typically several times a week. The time interval for wearing the gloves can also be increased, up to between 60 and 90 minutes, if desired, preferably repeating the misting of the gloves every 15 minutes or so.

Further in accordance with the invention, additional ingredients can be optionally incorporated in the original mixture of water and polyvinyl alcohol contained in the vat 12, to supplement and/or complement the basic moisturizing properties provided by the basic water/polyvinyl alcohol mixture as described in connection with the fabrication of the gloves as described above. The following constitute optional materials to be added to the polyvinyl alcohol/water solution either alone, or incombination with one another:

1. Phospholipid EFA, moisturizer, comprising Linoleamidopropyl PG-Dimonium Chloride Phosphate, in a quantity of up to 3% by weight, of the total mixture of water and polyvinyl alcohol.

2. AMG-O: Oleamidopropyl PG-Dimonium Chloride, a surfactant, in a quantity of up to 3% by weight, of the total mixture of water and polyvinyl alcohol.

3. Honey, in a quantity of less than 1% by weight, of the total mixture of water and polyvinyl alcohol.

4. AJIDEW N-50, comprising sodium PCA, a moisture retention salt, in a quantity of less than 1% by weight of the total mixture of water and polyvinyl alcohol.

5. VEGEPLEX 2500, a botanical extract complex, including extracts of Cranesbill, Comfrey, Elder Flower, Calendula, Tormentil, Plantain, Horsetail, Burdock, and Cucumber, in a quantity of less than 1% by weight of the total mixture of water and polyvinyl alcohol. These botanical extracts are considered to assist in the moisturizing process.

6. Aloe Vera, in a quantity of less than 1% by weight, of the total mixture of water and polyvinyl alcohol. The Aloe Vera is a moisturizer, and soothes and heals the skin.

7. PG 865, comprising propylene glycol, in a quantity of up to 2.5% by weight, of the total mixture of water and polyvinyl alcohol.

8. Vitamin C: Ascorbic Acid, in a quantity of up to 0.8% by weight, of the total mixture of water and polyvinyl alcohol.

9. Vitamin A, in a quantity of up to 0.25% by weight, of the total mixture of water and polyvinyl alcohol.

10. Vitamin E, in a quantity of up to 0.8% by weight, of the total mixture of water and polyvinyl alcohol.

As to the added benefits of the ten categories of ingredients listed immediately above, some or all of which may be included in accordance with the invention, as options, it is considered that the following specific effects are realizeable: Vitamin A helps to maintain healthy skin cell tissues and is used to restore damaged skin. It also retards aging of the skin. Vitamin C helps manufacture collagen and ensure collagen's strength. It has been shown to be capable of stimulating a fourfold increase in collagen synthesis. It further helps keep the skin soft, firm, supple, and wrinkle-resistant. Finally, the vitamin is an essential ingredient to any healing process.

Vitamin E prevents cell damage due to free-radicals. Vitamin E screens both UVB and phototoxic UVA rays, protecting the skin against sun damage, and helps heal previously damaged skin. It also tends to improve skin elasticity.

Botanical extracts such as Calendula, Comfrey, Cranesbill, Cucumber, Horsetail and Burdock enhance moisturization of the cells and accelerate microcirculation; they also tend to fight skin aging by improving the elasticity of the skin, and seek out free-radicals, as well as protecting against damage from pollution and ultraviolet rays.

Aloe Vera provides for soothing and healing of skin. Honey, when included in the initial polyvinyl alcohol solution utilized to manufacture the gloves or appliques, facilitates shaping of the gloves to the hands, thereby enhancing absorption of the water and other ingredients into the skin.

Sodium PCA tends to capture moisture, and retain it in the skin cells themselves.

Phospholipids bind moisture and proteins to the cell structure of the skin and nails, promotes fast absorption of the ingredients contained in the glove mesh, increases microcirculation in the skin, and promotes flow of nutrients to the skin cells.

Figure 2:
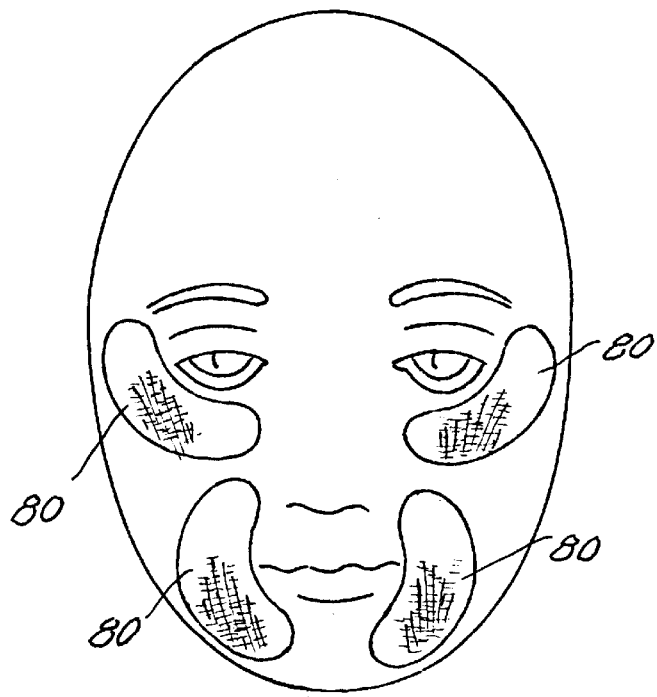
FIG. 2 is a diagrammatic representation of a person's face, and showing water-activatable appliques in the form of kidney-shaped patches in position on the skin and located at the corners of the mouth and immediately underneath the eyes. The patches constitute another embodiment of the invention.

FIG. 2 illustrates a series of patches 80 applied to a person's face, in accordance with the principles of the invention. Each patch preferably is constituted as a mesh or scrim, manufactured in accordance with the illustration of FIG. 4, so as to produce a porous, single-layer sheet having solidified polyvinyl alcohol on its surface and in its pores. Such patches are especially convenient for use in localized areas. In practice, the skin can be wetted first, and the patches 80 directly applied to the wetted skin. The polyvinyl alcohol component of the patch will start to dissolve in the presence of the water, and the patch will adhere by capillarity. Incidental wrinkles in the patch can be smoothed out readily, using the tips of the fingers.

Figure 3:
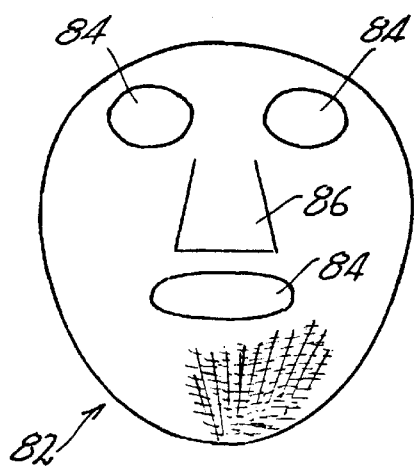
FIG. 3 is a plan view of a face mask constituted as an apertured water-activated moisturizing sheet adapted to be placed over the face, constituting yet another embodiment of the invention.

FIG. 3 illustrates another embodiment, depicting a face mask designated 82, having cutouts 84 for the eyes and mouth, and a slit 86 for the nose. The flap formed by the slit 86 can be easily wrapped onto the contour of the bridge of the nose, and around the nostrils, if desired.

Again, the mask is preferably a single-layer mesh impregnated with polyvinyl alcohol, which dissolves upon contact with water on the skin, where the skin has been wetted first.

Optionally, periodic re-application of moisture from a mist bottle, will rejuvenate the action of the patch, glove or mask, and enhance the basic moisturizing action on the skin.

From the above it can be seen that I have provided a novel and improved therapeutic applique, which is especially simple in its structure, and which has been found to be highly effective in imparting moisture to the skin. Essentially the applique utilizes a polyvinyl alcohol-impregnated mesh, with the polyvinyl alcohol in a dry state prior to use.

The dry state is important for shipping and storage, due to the fact that bacteria have great difficulty surviving in a largely dry environment. Thus, in this respect, the applique of the invention is unique when considered in the light of the numerous lotions and creams that are currently available, all of which possess the required moisture characteristics necessary to support copious amounts of bacteria, and thus require the addition of preservative chemicals. Moreover, these chemicals must be sufficiently strong to kill off such bacteria, and on a continuing basis.

This consideration of wet-based lotions, in contrast to a dry storage of the appliques of the present invention, is thus important in that with applicant's arrangement, the need for preservative is substantially completely eliminated. Thus, with the appliques of the present invention, there can occur absolutely no irritation of a type arising from contact with a preservative, (which in effect, is a mild form of a poison.) This feature is very beneficial for people who have sensitive skin, and/or who are allergic to preservatives. In some cases of dry, chapped hands, the condition is such that they are cut and/or bleeding. Under such circumstances, the fewer the ingredients which might be irritating, the better. Optimally, inclusion of only those ingredients that moisturize, soothe and heal, and perform a beneficial function, should be included in a skin care product. Preservatives are to be avoided. These objectives are effectively accomplished by the present invention.

The disclosed products and methods are thus seen to constitute a distinct advance and improvement in the field of skin moisturization and general skin care.

Variations and modifications are possible without departing from the spirit of the invention.

Each and every one of the appended claims defines an aspect of the invention which is separate and distinct from all others, and accordingly it is intended that each claim be treated as such when examined in the light of the prior art devices in any determination of novelty or validity.

What is claimed is:

1. A method of manufacturing a therapeutic glove for the treatment of dry hands, comprising the steps of:
   a) mixing a quantity of water with polyvinyl alcohol and heating the mixture while stirring it so as to dissolve the polyvinyl alcohol in the water and form a solution therewith,
   b) applying some of said solution to a backing paper so as to form a wet coating of the solution on the paper,
   c) laying a mesh onto the wet backing paper so as to be superposed thereon and to force some of the polyvinyl alcohol solution into the spaces of the mesh to impregnate the same,
   d) heating the superposed backing paper and mesh so as to evaporate water therefrom and solidify the polyvinyl alcohol at the same time that the mesh and backing paper are still superposed, said superposed backing paper and mesh forming an assemblage, and including the further step of placing one such assemblage on top of another such assemblage so as to respectively constitute palm and back-of-the-hand panels of a glove, with the meshes in superposed relation facing and touching each other, and
   e) simultaneously die-cutting and heat-fusing the superposed assemblages along an outline of a glove so as to produce a glove from the superposed assemblages, and including the further step of peeling off the backing paper from each mesh so as to leave as a residue in the respective mesh, the solidified polyvinyl alcohol.

2. The method of manufacturing a therapeutic glove for the treatment of dry hands as set forth in claim 1, and comprising the additional step of packaging the glove in an airtight container, to minimize exposure of the glove to moisture, and thereby maintain the solid polyvinyl alcohol in a dry, inactive state, until the glove is ready to be removed from the container and applied to the hand of the user.

3. The method of manufacturing a glove as set forth in claim 1, wherein the polyvinyl alcohol is added to the water in granular form, and the resulting mixture is heated to a temperature of up to 165 degrees F.

4. The method of manufacturing a glove as set forth in claim 3, wherein the mixture of polyvinyl alcohol and water is heated and mixed for a period of from 3 to 4 hours.

5. The method of manufacturing a glove as set forth in claim 1, wherein:
   a) the step of impregnating the porous sheet comprises the step of first applying the solution to and spreading it on the backing paper to a predetermined thickness just after the solution has been applied thereto, and
   b) thereafter forcefully applying the mesh onto the backing paper to cause the solution to impregnate the pores of the mesh.

6. The method of claim 5, and wherein the backing paper is a silicone coated material.

7. The method of claim 2, wherein the container is heat-sealed to shield the glove from moisture, thereby rendering inactive, the polyvinyl alcohol on the glove until after the container is opened by the consumer.

8. The method of claim 1, wherein the therapeutic glove is devoid of preservative chemicals of any kind.

9. The method of claim 1, wherein the thickness of the solution on the backing paper is on the order of several thousandths of an inch.

10. A method of manufacturing a therapeutic glove for the treatment of dry hands, comprising the steps of:
    a) mixing a quantity of water with polyvinyl alcohol and heating the mixture while stirring it so as to dissolve the polyvinyl alcohol in the water and form a solution therewith,
    b) applying some of said solution to a backing paper so as to form a wet coating of the solution on the paper,
    c) laying a mesh onto the wet backing paper so as to be superposed thereon and to force some of the polyvinyl alcohol solution into the spaces of the mesh to impregnate the same,
    d) heating the superposed backing paper and mesh so as to evaporate water therefrom and solidify the polyvinyl alcohol at the same time that the mesh and backing paper are still superposed,
    e) thereafter peeling off the backing paper from the mesh and leaving as a residue the solidified polyvinyl alcohol in the mesh,
    f) the step of impregnating the porous sheet comprising the step of first applying the solution to and spreading it on the backing paper to a predetermined thickness just after the solution has been applied thereto,
    g) thereafter forcefully applying the mesh onto the backing paper to cause the solution to impregnate the pores of the mesh, and
    h) heat fusing the superposed assemblages along a curved line having the outline of a glove, so as to fuse the assemblages at the locations of said outline.

11. A method of manufacturing a therapeutic glove for the treatment of dry hands, comprising the steps of:
    a) mixing a quantity of water with polyvinyl alcohol and heating the mixture while stirring it so as to dissolve the polyvinyl alcohol in the water and form a solution therewith,
    b) applying some of said solution to a backing paper so as to form a wet coating of the solution on the paper,
    c) laying a mesh onto the wet backing paper so as to be superposed thereon and to force some of the polyvinyl alcohol solution into the spaces of the mesh to impregnate the same,
    d) heating the superposed backing paper and mesh so as to evaporate water therefrom and solidify the polyvinyl alcohol at the same time that the mesh and backing paper are still superposed, and
    e) thereafter peeling off the backing paper from the mesh and leaving as a residue the solidified polyvinyl alcohol in the mesh,
    f) the step of impregnating the porous sheet comprising the step of first applying the solution to and spreading it on the backing paper to a predetermined thickness just after the solution has been applied thereto, and followed by the step of
    g) forcefully applying the mesh onto tie backing paper to cause the solution to impregnate the pores of the mesh, h) the backing paper being a silicone coated material, and wherein the porous mesh and backing paper constitute an assemblage, and including the further step of placing one such assemblage on top of another assemblage, with the meshes in superposed relation facing and touching each other, and thereafter die-cutting the superposed assemblages into glove-shaped forms, and i) including the further step of die-cutting the superposed assemblages along a border outside of the fused outline, so as to form a blank constituting a glove.

12. The method of claim 6, and including the further step of removing the backing paper from the glove.

* * * * *